(12) United States Patent
Sharkey

(10) Patent No.: US 6,246,913 B1
(45) Date of Patent: Jun. 12, 2001

(54) METHOD AND APPARATUS FOR THE TREATMENT OF STRABISMUS

(75) Inventor: Hugh R. Sharkey, Woodside, CA (US)

(73) Assignee: Oractec Interventions, Inc., Menlo Park, CA (US)

( * ) Notice: Subject to any disclaimer, the term of this patent is extended or adjusted under 35 U.S.C. 154(b) by 0 days.

(21) Appl. No.: 09/171,213

(22) PCT Filed: Feb. 12, 1998

(86) PCT No.: PCT/US98/02860
§ 371 Date: Oct. 13, 1998
§ 102(e) Date: Oct. 13, 1998

(87) PCT Pub. No.: WO98/34551
PCT Pub. Date: Aug. 13, 1998

Related U.S. Application Data

(60) Provisional application No. 60/038,023, filed on Feb. 14, 1997.

(51) Int. Cl.[7] .................................................. A61F 2/00
(52) U.S. Cl. .............................. 607/101; 606/4; 606/5; 606/41; 606/48; 606/50
(58) Field of Search ............................ 607/96, 98, 100, 607/101, 102; 606/41, 42, 45–52; 128/898

(56) References Cited

U.S. PATENT DOCUMENTS

| | | |
|---|---|---|
| 4,846,175 | 7/1989 | Frimberger . |
| 5,114,402 | 5/1992 | McCoy ................................. 604/95 |
| 5,152,748 | 10/1992 | Chastagner ............................ 604/95 |
| 5,242,441 * | 9/1993 | Avitall .................................. 606/41 |
| 5,279,559 | 1/1994 | Barr ...................................... 604/95 |
| 5,364,395 | 11/1994 | West, Jr. . |
| 5,415,633 | 5/1995 | Lazarus et al. ....................... 604/95 |
| 5,433,739 | 7/1995 | Sluijter et al. ........................ 607/99 |
| 5,776,176 * | 7/1998 | Rudie .................................. 607/101 |
| 5,916,214 * | 6/1999 | Cosio et al. .......................... 606/41 |
| 5,921,982 * | 7/1999 | Lesh et al. ............................ 606/41 |
| 6,033,403 * | 3/2000 | Tu et al. ............................... 606/41 |

FOREIGN PATENT DOCUMENTS

| | | |
|---|---|---|
| 39 18316 | 3/1990 | (DE) . |
| 0 682 910 A1 | 11/1995 | (EP) . |
| 0 737 487 A2 | 10/1996 | (EP) . |
| 2 645 008 | 10/1990 | (FR) . |
| WO 82/02488 | 8/1982 | (WO) . |
| WO 92/05828 | 4/1992 | (WO) . |
| WO 93/16648 | 9/1993 | (WO) . |
| WO 95/10981 | 4/1995 | (WO) . |
| WO 95/25471 | 9/1995 | (WO) . |
| WO 96/11638 | 4/1996 | (WO) . |
| WO 96/32885 | 10/1996 | (WO) . |
| WO 96/34559 | 11/1996 | (WO) . |
| WO 98/17190 | 4/1998 | (WO) . |

* cited by examiner

Primary Examiner—Linda C. M. Dvorak
Assistant Examiner—R. Kearney
(74) Attorney, Agent, or Firm—David J. Weitz; Wilson Sonsini Goodrich & Rosati

(57) ABSTRACT

A surgical heating probe, comprising a handle, a radio-frequency-shielded neck extending from the handle and having an unshielded cathode and an unshielded anode present in the neck with a shielded insulating section of the neck located between the cathode and the unshielded anode, the neck being formed so that three points located in the cathode, the anode, and the insulating; section, respectively, form a triangular plane, the cathode, the anode, and the insulating section being spaced apart at distances adapted so that the cathode and the anode can closely approach opposite sides of an animal tendon, and an energy connector fixture located in the handle and adapted to connect a supply of heating energy to the anode and the cathode. The probe is particularly useful for the treatment of strabismus, and the invention involves the use of radio frequency heating to shrink extraocular tendons in the treatment of strabismus.

10 Claims, 13 Drawing Sheets

Oblique View of Ex Vivo Eye Model

Cross-Section of Ex Vivo Eye Model

METHOD AND APPARATUS FOR THE TREATMENT OF STRABISMUS

This application claims benefit of provisional application No. 60/038,023, filed Feb. 14, 1997. This application is a 371 of PCT/US98/02860 filed Feb. 12, 1998.

BACKGROUND OF THE INVENTION

1. Technical Field

This invention is directed to the field of ophthalmic surgery and is specifically directed to methods for the relief of strabismus by the retensioning of ocular muscles using radio frequency modification of collagen in tendons.

2. Background

Strabismus is a misalignment between the two eyes such that the two visual axes do not intersect the point of regard. Between one and four percent of the childhood population is effected by strabismus. "The annual number of surgical operations for strabismus (close to 700,000 or 11 percent of all ophthalmic procedures) is exceeded only by cataract surgery . . . " (National Advisory Eye Council, 1994). Typically, onset is in childhood, but can occur later in life due to lesions in the oculomotor pathway.

Correction of misalignment early in life is central to the development of normal binocular vision and the prevention of amblyopia. Accordingly, strabismus surgery is performed as early in life as possible, and is typically performed under general anesthesia in children and most adults.

In 20% to 50% of patients, repeat surgery is required due to post-operative under- or overcorrection. Repeat surgery places the patient at additional per procedure risk. In addition, secondary surgical procedures are often complicated by the presence of scar tissue and tissue adhesions, with the outcomes being compromised accordingly.

Conventional surgical procedures strengthen the action of an extraocular muscle by resection, advancement, and tucking of the extraocular muscle. In each instance, the muscle's tendon is cut free of the eye at its insertion into the sclera and then sutured back onto the globe. The muscle's tendon may be shortened by cutting off a predetermined amount.

Surgically weakening the action of an extraocular muscle, which is often done in conjunction with strengthening the action of the antagonist, will consist of one of two basic approaches. In one approach the muscle insertion is cut and sutured to the eye at a more posterior position. In the other approach, marginal myotomy, incisions are made part way through the tendon such that the tendon is thinned and elongated.

In the past few years crystallized botulinum toxin, which acts by blocking the release of acetylcholine at the neuromuscular junction, has been used for the temporary partial paralysis of the extraocular muscles. The therapeutic effect with this treatment modality is variable and decreases over time.

Risks associated with conventional strabismus surgery include perforation of the globe when suturing the tendon; variable motor effectiveness, due to the difficulty in quantifying tucking, resection, advancement, and recession procedures; tissue scaring; and tissue adhesions.

Accordingly, there is a need for new surgical techniques and apparatuses that simplify surgical operation and reduce risks associated with strabismus surgery.

SUMMARY OF THE INVENTION

It is an object of the present invention to provide a technique for correcting strabismus that does not require surgical incision of extraocular muscle tendons.

It is a further object of the invention to provide an electrosurgical apparatus satisfactory for use in strabismus.

These and other objects of the invention have been accomplished by a surgical heating probe, comprising a handle, a radio-frequency-shielded neck extending from the handle and having an unshielded cathode and an unshielded anode present in the neck with a shielded insulating section of the neck located between the cathode and the unshielded anode, the neck being formed so that three points located in the cathode, the anode, and the insulating section, respectively, form points of a triangular plane, the cathode, the anode, and the insulating section being spaced apart at distances adapted so that the cathode and the anode can closely approach opposite sides of an animal tendon, and an energy connector fixture located in the handle and adapted to connect a supply of heating energy to the anode and the cathode. The probe is particularly useful for the treatment of strabismus, and the invention preferably involves the use of radio frequency heating to shrink or loosen extraocular tendons in the treatment of strabismus.

BRIEF DESCRIPTION OF THE DRAWINGS

The invention now being generally described, the same will be better understood by reference to the drawings that form part of this specification, wherein.

DESCRIPTION OF SPECIFIC EMBODIMENTS

Figure 1:
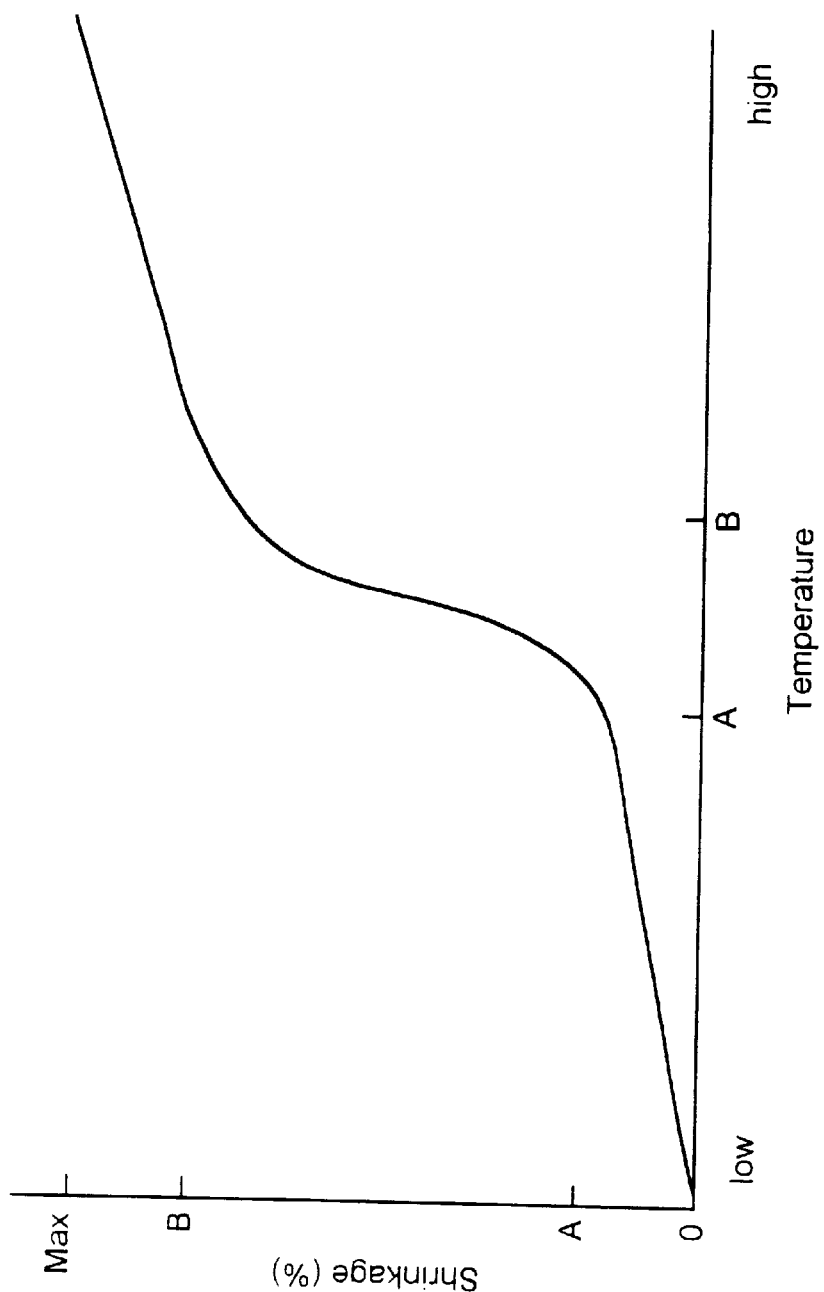
FIG. 1 is a graph showing collagen shrinkage as a function of temperature.

The present invention uses thermal, usually radio frequency (RF) energy, to safely shrink extraocular muscle (EOM) tendon, thus providing a minimally invasive procedure for correcting extraocular muscle imbalances that avoids surgical incisions now commonly used. Sufficient heat can be selectively focused on the extraocular muscle tendon using an EOM heating apparatus of the invention to denature the constituent collagen while maintaining safe temperatures in the surrounding tissues, an important part of the present invention not previously known in the art. An EOM heating apparatus of the invention typically consists of an RF generator, a delivery hand piece, and a cooling mechanism. Previously in the laboratory of inventors, an RF generator for bipolar electrode catheters was developed that delivers hyperthermia doses to internal body regions in a manner that is minimally invasive. This generator can be used to power the EOM hand-piece electrodes of the invention, or other generators having the same features can be specifically designed for this use or modified from existing generators. A commercially available irrigation pump can be used to cool the EOM hand piece described below, or other existing or newly developed hand pieces can be used (usually with modification unless developed specifically for strabismus) in the manner described below.

The shrinkage vs. temperature characteristics of the eye tissues, the heat distribution produced by various EOM hand-piece configurations within the tissue preparation, and the time vs. temperature shrinkage characteristics of the eye tendons and other tissue when treated with an EOM radio frequency heating element, along with the benefits of a range of static and dynamic therapeutic protocols in optimizing the target tissue to surround tissue temperature ratios, are discussed below. Therapeutically meaningful shrinkage of the extraocular muscle tendon can take place while surrounding tissue temperatures are kept below 45° C., so that the surrounding tissue histology is maintained in its normal state.

Before turning to a detailed description of a specific radio frequency handheld probe of the present invention designed specifically for strabismus, a brief review of extraocular muscle structure and function will be helpful for those working in the field of radio frequency ablation and similar medical devices who are not familiar with this new field to which RF modification is being applied. There are six extraocular muscles attached to the globe of the eye that control the orientation of the eye within the orbit. The four rectus muscles originate at the back of the orbit from the annulus of Zinn and transverse the orbit to insert into the globe several millimeters behind the limbus. The superior oblique muscle originates from just outside the annulus of Zinn. Its long tendon passes through the trochlea that is attached to the frontal bone a few millimeters from the orbital margin and is reflected back to make a wide insertion in the outer posterior superior quadrant of the globe. The inferior oblique muscle originates from the floor of the orbit just within the orbital margin and inserts into the globe in the outer posterior inferior quadrant of the globe.

The lengths and widths of the extraocular muscle tendons at the globe are given in Table 1.

TABLE 1

| Muscle | Tendon Length (mm) | Tendon Width (mm) |
| --- | --- | --- |
| Medial Rectus | 4 | 10.3 |
| Lateral Rectus | 7–9 | 9.2 |
| Superior Rectus | 6 | 10.6 |
| Inferior Rectus | 5.5 | 9.8 |
| Superior Oblique | 20 | 10 |
| Inferior Oblique | <2 | |

Sources: Spooner, 1957 and McCotter, 1949

The tendons of the four rectus muscles are accessilble via the palpebral aperture. During surgery a muscle hook (commonly used in existing strabismus surgery involving incisions) is used to identify and isolate these tendons.

The lateral and medial recti are associated with esotropia and exotropia and are readily accessed by superficial dissection of the overlying conjunctiva and Tenon's capsule. Accordingly, tension in these muscles is easily corrected by the methods of the invention.

Tendons in their normal state consist of regularly arranged bundles of collagen that generally run parallel to each other. When heated above a threshold temperature, these bundles of collagen lose their regularity, become denatured, and bunch up. The degree of bunching, and hence of shrinkage of the tendon, is dependent upon the temperature to which the tissue is heated.

FIG. 1 shows a theoretical shrinkage vs. temperature collagen curve for collagen not under tension when heated (Danielsen, 1981; Danielsen, 1994). These shrinkage functions were obtained by gradually increasing the temperature of a saline bath surrounding the test tissue but can also be used to guide the process of the invention, as temperatures of tissue can be measured with a temperature probe during the procedure. The shrinkage curve is divided into three parts. There is a linear part before transition, i.e., at temperatures below $T_A$ of FIG. 1, and a linear part after transition, i.e., at temperatures above $T_B$. The transition region is between temperatures $T_A$ and $T_B$. The shrinkage due to transition is the difference between $S_A$ and $S_B$ and accounts for the majority of the shrinkage that takes place in the tissue.

The values of $T_A$, $T_B$, $S_A$, and $S_B$ in collagen shrinkage curves depend on a host of histological factors, the time course of heat treatment (Fanton et al., 1997), and whether or not the tissue is under tension when heated. Reported shrinkage-curve constant values correspond to values observed in research in the laboratory of the inventors on collagen secured from human cadaver ligaments. Values for $S_A$ range from 10 to 20 percent. Values for $S_B$ range from 60 to 80 percent. Values for $T_A$ range from 52° C. to 60° C. with the difference between $T_A$ and $T_B$ being approximately 4° C. to 5° C.

Figure 2A:
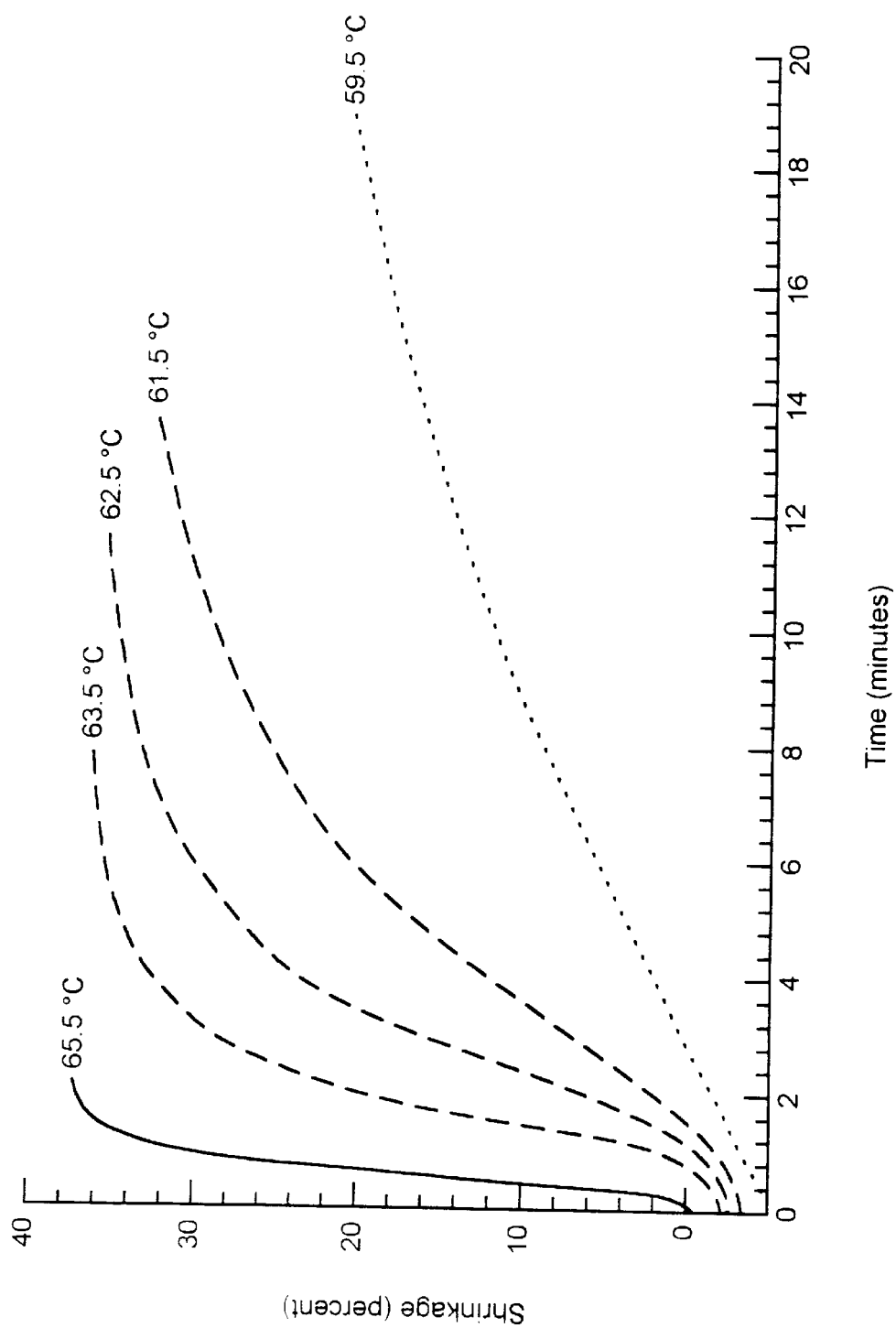
FIGS. 2A–C are graphs showing collagen: Shrinkage vs. Time, Stress vs. Stretch Ratio, and Stress vs. Strain.

FIG. 2A shows representative model functions for bovine extensor tendon for shrinkage vs. time. Studies of the thermal response of collagenous tissue show that tissue shrinkage increases as a function of time when the tissue temperature is less than $T_B$. The lower the temperature, the longer the tissue shrinkage takes to reach its steady state shrinkage end point. Tissue heated to temperatures near $T_A$ take on the order of 20 minutes to stabilize, while tissue heated to near $T_B$ stabilize in less than 0.5 minute (Fanton et al., 1997). Percent shrinkage (of the entire tendon) will also depend on the area of an EOM tendon being treated, which will depend both on the apparatus being used and the techniques of the surgeon using the apparatus.

The temperature time behavior of collagen shrinkage provides a precise controlling of the therapeutic effect of hyperthermia treatment. The treatment region can be designated preoperatively and the hyperthermia dose set so as to achieve a specified amount of tendon shrinkage within a specified treatment time period. Accordingly, as discussed below, one of the goals for optimal operation of this procedure is to establish temperature and time shrinkage curve constants for extraocular muscle tendons in mammalian eyes for any specific heating element being used.

FIG. 2A. Plot of shrinkage versus time for various constant temperatures as predicted by model fit to experimental data. The slope of each line represents the shrinkage "rate."

Note the extreme sensitivity of shrinkage rate to temperature changes.

$$\text{Shrinkage}(t, T) = \frac{(0.53T - 70.09)}{1 + \left(\frac{t}{4.0c^{(29.76-0.487)}}\right)^{(0.38T-21.31)}} + 35.35$$

Figure 2B:
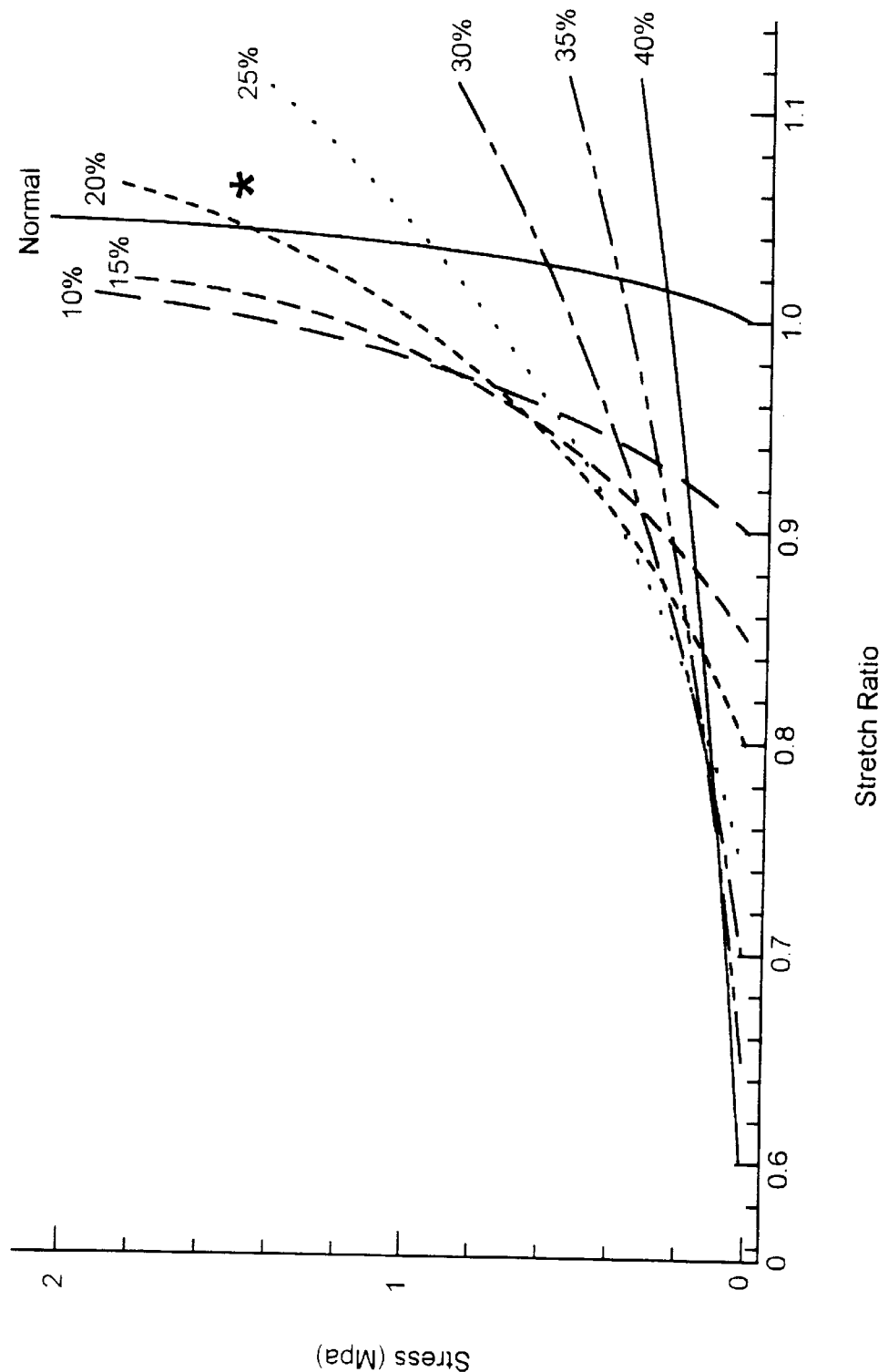

FIG. 2B. Plot of stress versus "stretch ratio." Asterisk (*) indicates intersection of 20% shrinkage curve with normal tendon curve. At this shrinkage percent, the tissue is so extendible that it elongates beyond the normal tendon, despite starting from a "contracted" state.

Figure 2C:
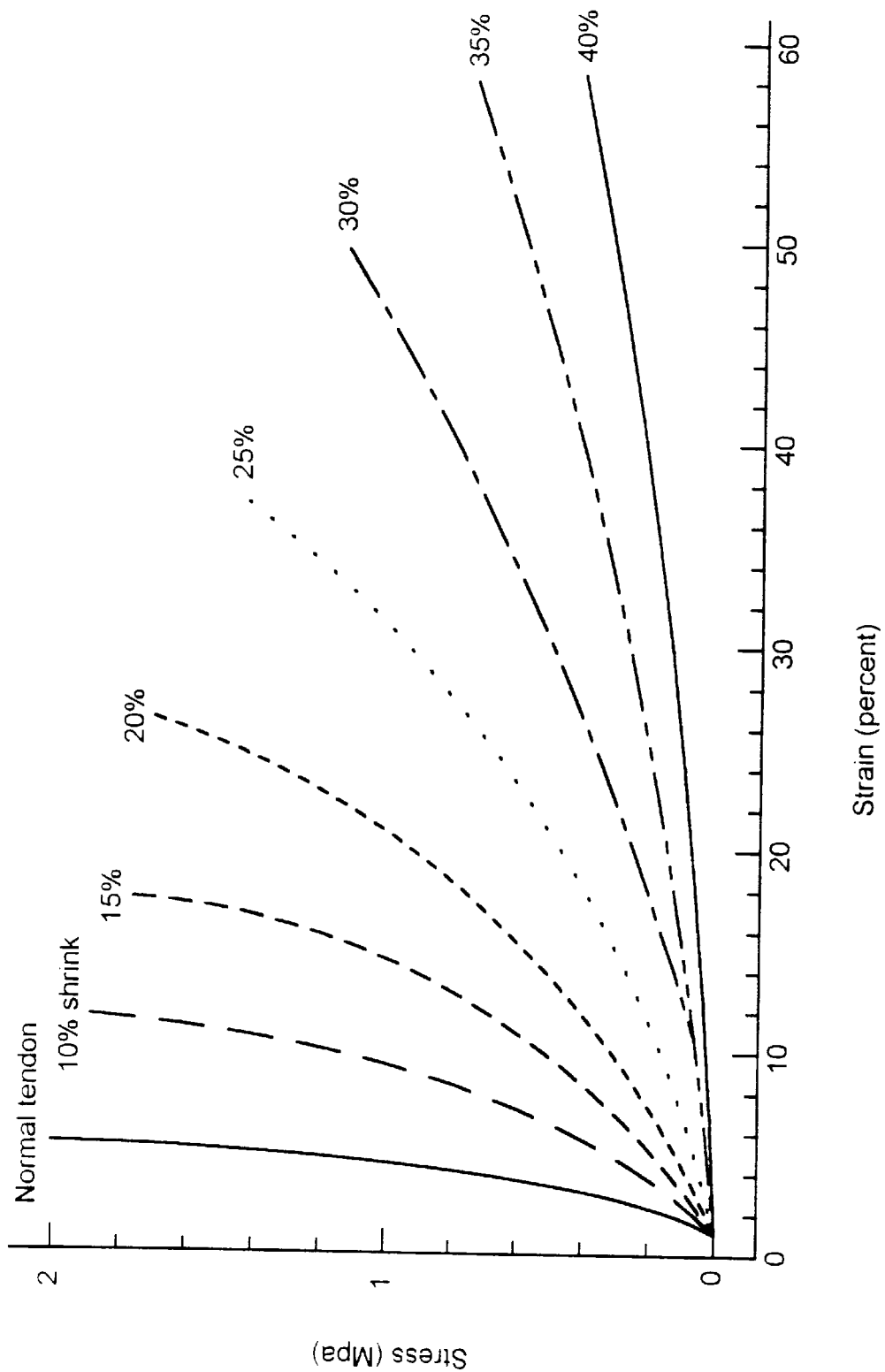

FIG. 2C. Family of curves produced by plotting stress versus strain for increasing percent shrinkage as predicted by model fit to experimental data. For the equation: stress ($\sigma$, in MPa), strain ($\epsilon$, in percent) and shrinkage (S, in percent).

Tendon Shrinkage

Tendon shrinkage was found to be a function of time and temperature, as shown in FIG. 2A. At any given temperature, the shape of the shrinkage versus time response was sigmoidal, with an initial region of slow change, followed by an increase in shrinkage rate, and finally, a plateau to maximal shrinkage. While the rates of shrinkage at each temperature were reproducible there was variability in the maximal shrinkage achieved. There was no significant statistical correlation between the independent parameters of temperature, time, initial area and preload and the dependent variables of maximal shrinkage and final area. The variability in maximal shrinkage was attributed to specimen variability. The mean maximal shrinkage was 30.6±7.3%.

A seven parameter logistic equation (sigmoidal function) was used to model the experimental data for shrinkage (S, in percent) as a function of time (t, in minutes) and temperature (T, in ° C.):

$$S(t, T) = \frac{[a_0(T - 62) + a_1] - a_2}{1 + \left(\frac{t}{a_3 e^{-a[T-62]}}\right)^{[a_4(T-62)+a_5]}} + a_2 \quad (1)$$

where a, $a_0$, $a_1$, $a_2$, $a_3$, $a_4$, and $a_5$ are constant coefficients. Equation (1) was curve fit to all of the experimental data simultaneously (N=29) to determine the coefficients. The values for a, $a_0 a_1 a_2$, $a_3$, $a_4$, and $a_5$ were 0.48±0.01/° C., 0.53±0.21%/° C.,−1.88±0.39%, 35.35±0.31%, 4.00±0.07 minutes, 0.38±0.04/° C., and 2.25±0.07, respectively (±SE). A plot of shrinkage versus time for the temperatures used is shown in FIG. 2A. Equation (1) can be used to predict shrinkage under given time and temperature conditions.

Tendon Mechanical Properties

As the tendon shrunk, the cross sectional area increased and the mechanical properties decreased. The change in the mechanical properties was found to be independent of the method used in achieving the shrinkage, that is, the stress-strain response for a specimen shrunken by 20% through heating at high temperature and a short period of time was the same as that obtained by heating at a lower temperature and a longer period of time. The primary factor influencing changes in the mechanical response was the amount of tendon shrinkage and not the method used to achieve this shrinkage.

To model the mechanical response, a relationship was derived between the stress ($\sigma$, in MPa) and strain ($\epsilon$, in percent) as a function of shrinkage (S, in percent), given by:

$$\sigma(\epsilon, S) = [b_0(S-20)+b_1](e^{[b_2 e^{-b(S-20)}]\epsilon} - 1) \quad (2)$$

in which the coefficients b, $b_0$, $b_1$, and $b_2$ are constant coefficients. Equation (2) was curve fit to all the experimental data (N=58) to solve for the unknown coefficients. The values for b, $b_0$, $b_1$, and $b_2$ are 0.095±0.0.003/%, 0.008±0.002 MPa/%, 0.42±0.025 MPa, and 0.061±0.0023, respectively (±SE). A family of curves representative of the stress-strain response as a function of shrinkage is shown in FIG. 2C. Progressive shrinkage resulted in the tendons becoming more extendible. There was a progressive increase in the toe region and decrease in the slope (modulus) of the linear region.

Structural Alterations

Transmission electron microscopy (TEM) of representative samples of normal bovine tendon and tendon heated to 65, 70, and 80° C. showed the classic cross striations characteristic of collagen molecules in their native organized ("crystalline") and extended conformation. With heating there was a progressive increase in the percentage of collagen fibrils that lost their cross striations as the crystalline organized structure was denatured to a contracted, random coil conformation. The margins of the denatured fibrils were still recognizable in the specimens heated to 65 and 70° C. but were lost in the 80° C. specimens, the later having an amorphous appearance (gelatin).

With increasing shrinkage, a higher proportion of the collagen fibrils underwent the conformation change from an extended, crystalline, inextendible state to that of a contracted, random coil, extendible state. Transmission electron microscopic photographs provide evidence of the changes taking place at the structural level that are responsible for the observed mechanical property changes.

The disruption of the normal orientation of the collagen fibrils subsequent to heat treatment leads to initial weakening of the tissue as well as shrinkage, which can be selectively used to lengthen as well as shorten an ocular tendon. The degree of tissue weakening depends on the percent shrinkage rather than the time or temperature used to accomplish the shrinkage. Progressive shrinkage results in the tendons becoming more extendible, with sufficient stress leading to the tissue extending out to its pre-treatment dimensions (Fanton et al., 1997). This extensibility attribute of heated tissue persists until the tissue heals and the collagen which forms the tissue has normal strength and no longer has a tendency to stretch under tension. Experiments performed at the laboratories of the present inventors on rabbits show that healing takes place in about six weeks, after which the tissue has regained its full strength. Ongoing experiments on sheep confirm these results.

This extensibility of the tissue may place a constraint on the amount to which a given tendon can be shrunk in a single procedure, or may require that dissolvable traction sutures be in place during the healing period, if the object of a particular operation is to shorten rather than lengthen a tendon. Data involving heating of collagen under other circumstances indicates that the healing period in humans should be less than 60 days, after which the tissue is expected to be at full strength and repeat procedures could be performed. The healing period can be shorter, as patients treated with hyperthermia to injured shoulder ligaments demonstrate normal use of the joint in 10 to 14 days.

Post-hyperthermia-treatment tissue extensibility and the maximum shrinkage response of the extraocular muscle tendons define the amount of ocular realignment that can be gained using an EOM heating element and procedure of the invention. An early study on monkey eyes using a radio frequency heating source to shrink tendons suggests that tissue shrinkage of about 80 percent of total tendon length may be obtained in a single dose. In that study, hyperthermia was applied using only gross observation of tissue response and appearance to determine the hyperthermia dose. Shrinkage of about 4 mm for the medial rectus muscles and 6 mm for the lateral rectus muscles has been reported. Qualitative postoperative testing of the treated eye using forced ductions and tension placed by capture and rotation of the muscles on a muscle hook indicated that the strength of the tissue was normal for these amounts of shrinkage (Finger et al., 1987).

If the eye is assumed to be a 24 mm diameter sphere, and the region of treatment is assumed to correspond to the periphery of the sphere, about 4.8° of correction is achieved for each 1.0 mm of muscle shortening. Thus, up to 19.2° of correction may be achievable with medial rectus hyperthermia treatment and 28.8° of correction may be achievable with lateral rectus hyperthermia treatment. Such corrections will alleviate strabismus of the majority of potential patients.

Turning now to the specifics of RF heating, localized radio-frequency-induced hyperthermia has been known for over 30 years (see, for example, U.S. Pat. No. 4,043,342 and the publications listed therein), so that only a general description of the overall process is set forth here for those not familiar with the technique. Localized hyperthermia is created by passing a current between two electrodes positioned on opposite sides of the target tissue. Radio-frequency-induced heating is generally done using currents oscillating at frequencies up to 100 MHz. Tissue heat is created by the resistance to the current flow created by the extracellular ions. This is in contrast to microwave heating, i.e., above 300 MHz, which creates heat by both extra- and intracellular ion resistance.

Several parameters govern the distribution of the: temperature throughout the tissue heated by means of resistive RF current. Distribution of the power deposition is one of the most important parameters. It is expressed either per unit volume (absorption rate density (ARD) in W m$^{-3}$) or per unit mass (specific absorption rate (SAR) in W kg$^{-1}$). The ARD and SAR are similar for most tissues. Thus, three operational issues are important to the heat distribution between and around two RF electrodes:

The voltage applied to the electrodes.

The electrical conductivity of the tissue.

The shape and size of the electrodes.

A sophisticated RF generator with thermal feedback control developed in the laboratory of the present inventors can deliver a precise voltage to the EOM electrodes and is the subject of earlier patent applications, as are other relevant systems in the field of electrosurgery. See, for example, U.S. Pat. No. 5,458,596; U.S. Pat. No. 5,569,242; and U.S. application Nos. 08/637,095, 08/714,987, 08/320,304, 08/547,510, 08/390,873, 08/616,752, 08/696,051, 08/700,195, 60/029,600, 60/029,602, 60/029,734, and 60/029,735. While this is the preferred amplifier because of the thermal feedback control that is available, other generators can be used (albeit with significantly greater danger and difficulty of operation) as long as temperatures and times are maintained in the ranges described in this specification or within the general parameters described here that allow design of similarly functioning electrodes.

The extraocular muscle tendons normally have uniform conductance. Therefore we anticipate that heating will occur uniformly within the tendon, although temperature probes in the tendon can be used if conditions are found to be different for a particular operation. The electrical conductivity of the tendons is similar to that of muscle, which has a conductivity of about $5.8 \times 10^{-3}$ mho-cm$^{-1}$ to $8.47 \times 10^{-3}$ mho-cm$^{-1}$ (Hahn et al., 1980, and Cosset et al., 1982, respectively). Although any newly designed hand piece can be initially operated under the conditions described in this specification (with empirical adjustment of conditions, if necessary), the thermal distribution within the tendons and the surrounding tissue is preferably determined for each electrode handpiece.

Sensitive neighboring structures in the region of the eye include the orbital fat, sclera, conjunctiva, cornea, blood vessels, and orbital bone. The orbital fat, anterior ciliary arteries and veins, conjunctiva, and sclera will be in close juxtaposition to the EOM electrodes, and, as discussed below, these sensitive tissues should be protected from hyperthermia. The surrounding orbital bone does not impose any unique design requirements on the EOM heated region, as it is a poor heat conductor and, for a rotated eye, removed from the therapeutic site by several millimeters.

The size and shape of the electrodes can be used to advantage to focus and distribute the heat generated by the extracellular current. For equally sized electrodes that are imbedded in a uniform conducting tissue the current density is equal in the vicinity of each of the electrodes, and the tissue heats in a symmetrical fashion. When one electrode is larger than the other, the current density is lower in the vicinity of the larger electrode. Therefore the tissue will be hotter around the smaller electrode and cooler near the larger electrode.

Fluid flow around and through tissue will alter the heat distribution by its cooling effect. Blood flow through a tissue can alter the heat distribution, but studies show that vessel size must be substantially larger than the orbital blood vessels (Crezee, 1992). Should hyperthermia be a problem for a particular apparatus or because of the lack of proper feedback control, artificial irrigation of body lumens during hyperthermia treatment will protect surrounding tissue from receiving therapeutic dosage levels.

A fundamental concern when administering hyperthermia is the uniformity of the heat distribution within the target tissue and the extent of unwanted heating of surrounding tissue. RF-induced hyperthermia provides advantages over other heating techniques for treating the extraocular muscle tendons due to the ability to focus the hyperthermia dose on the tendons while controlling the unwanted heating of surrounding tissue.

Figure 3:
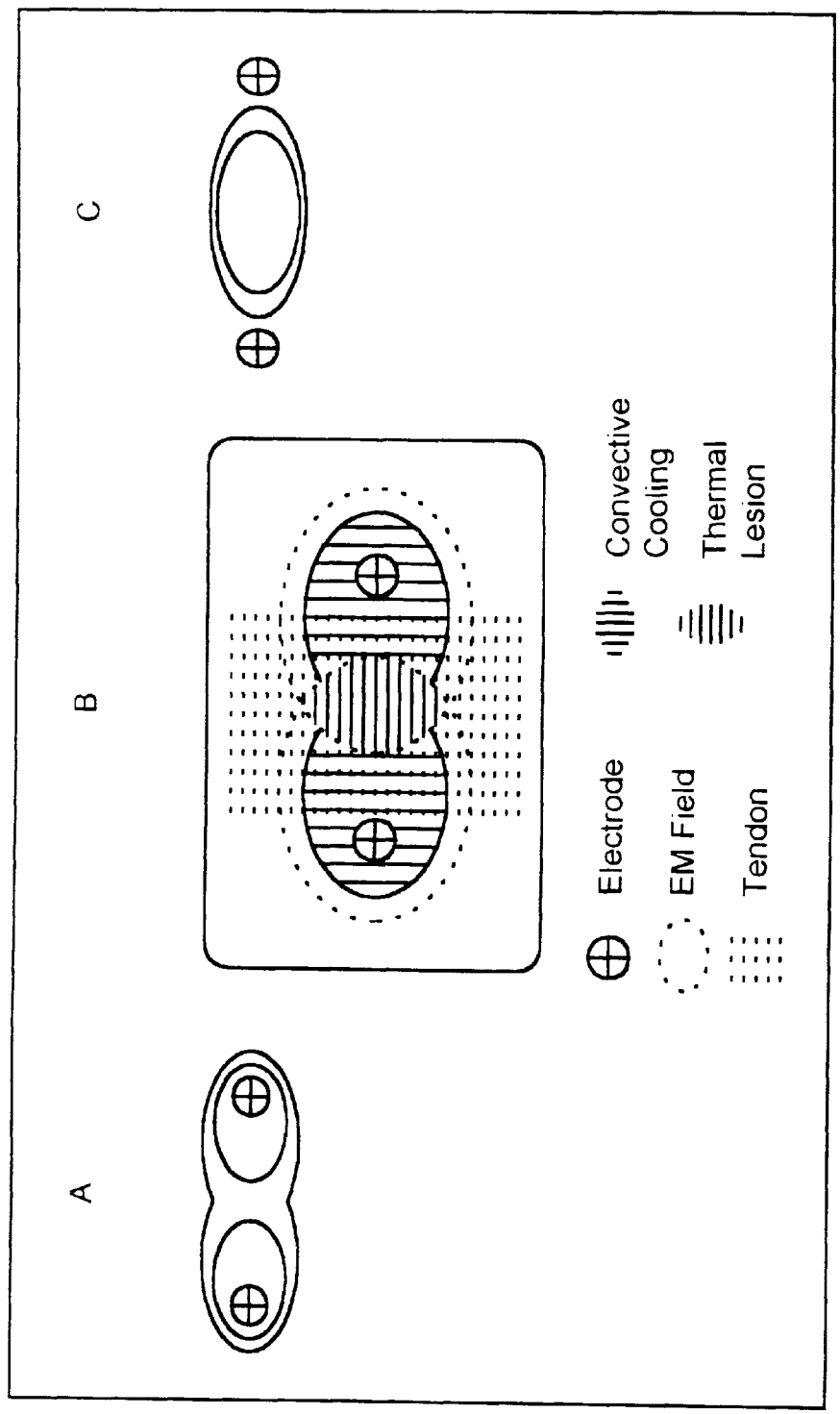
FIG. 3A is a diagram of theoretical isotherms for a conventional bipolar RF electrode configuration in perfused tissue.
FIG. 3B is a diagram depicting the interplay of cooling convective forces and electromagnetic induced tissue resistive heating resulting in a focused hot spot.
FIG. 3C is a diagram of theoretical isotherms for bipolar RF electrodes that are cooled.

Theoretical isotherms are shown in FIG. 3A for a conventional RF bipolar electrode configuration assuming that the contacted tissue has a uniform conductance and that there is blood flow through the tissue (Strohbehn, 1983, and Mechling, 1986). Since the treated portion of an extraocular muscle tendon will be dissected free of the orbital contents using standard techniques, the outer surfaces of the EOM electrodes will either not be in contact with any surrounding tissue or will be positioned within a cavity formed by manipulation of the ocular tissues. Accordingly, fluid flow through and around the electrodes can be used to reduce the heat transfer to the surrounding tissue while permitting the sandwiched tissue to selectively reach therapeutic heat levels. This is accomplished through the interaction of cooling convective forces and the restive heating generated by the electromagnetic fields, as shown in FIG. 3B. Theoretical isotherms with this cooled electrode configuration are shown in FIG. 3C. As discussed below, these thermal control mechanisms are incorporated into the design of the EOM electrodes.

The surgical dissection for using the EOM electrodes will be similar to that for conventional strabismus surgery. The approach is from the front via the palpebral conjunctiva, which is cut to reveal the tendon of the rectus muscle of concern. A muscle hook is then passed through Tenon's capsule under the tendon and used to hold the eye and delineate the tendon, which is cut free of surrounding tissue for its full length. For the medial and lateral rectus muscles, the ciliary arteries and veins are dissected free of the tendon.

Figures 4A, 4B:
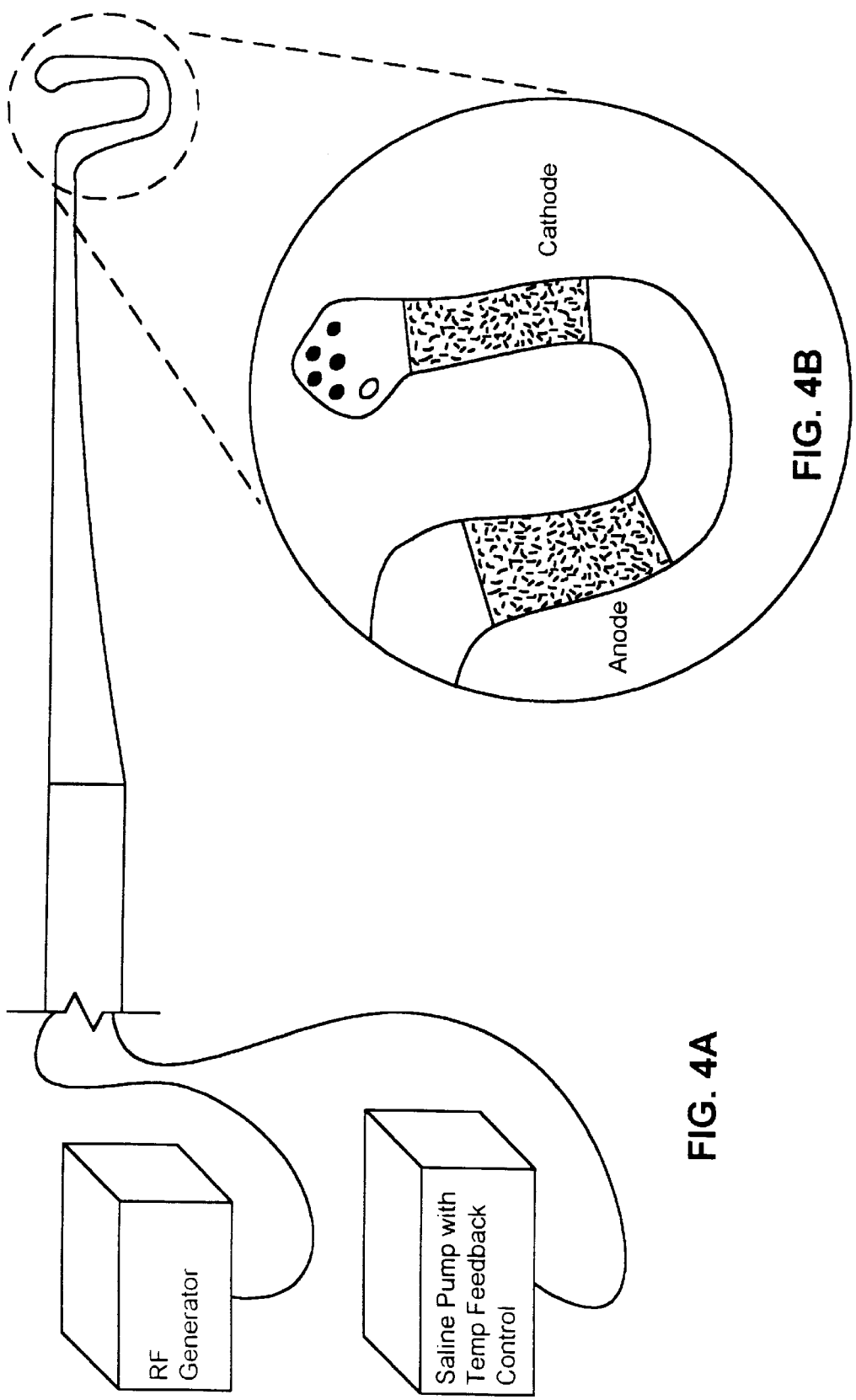
FIG. 4 is a schematic diagram showing a perspective view of a bipolar electrode of the invention designed for heating of an extraocular tendon.

A design for the EOM electrode is shown in FIG. 4. The hand piece is in the form of a U-shaped muscle hook that can catch and bracket a tendon. The opposing arms of the U are bipolar electrodes that deliver the RF energy. In preferred embodiments the shaft is hollow and provides at least one lumen through which fluid can be pumped to cool the instrument. The cooling mechanism will keep the electrodes cool, while simultaneously allowing the tendon, which is manipulated by the hand of the surgeon to be between the electrodes, to be heated by molecular friction. The cooling fluid can either be recirculated or allowed to exit the distal portion of the handle in order to irrigate and cool the surrounding tissue. Optionally, thermocouples could be placed at strategic points on the distal portion of the handle to provide feedback control of the RF generator, which is connected to the hand piece along with a fluid pump.

Accordingly, the EOM electrode design offers the following mechanisms that can be configured to optimize the therapeutic dose relative to unwanted surround tissue heating:

Temperature and flow of the cooling fluid can be controlled via thermal feedback, or adjusted manually.

Irrigation of the surround tissue can be accomplished through the hand piece, with the distribution of the irrigating fluid determined by the position of the exit ports.

Size and shape of the bipolar electrodes can be varied to modify the isotherms.

The RF energy can be feedback controlled or set to a predetermined level.

Heating the tissue for longer time intervals at lower temperatures can achieve shrinkage comparable to heating at higher temperatures for shorter durations. Therefore, extending the treatment time and reducing the RF energy is a possible means of assuring that the surrounding tissue is not heated, while simultaneously securing the desired therapeutic effect. Accordingly, shrinkage vs. time functions can be obtained as discussed below for an extraocular muscle preparation using any modification of the specific hand-operated electrode described in this specification in order to evaluate the utility of extended-time therapeutic protocols, and, hence, whether or not there would be need to develop specific surgical techniques for control of hand piece movement for any newly developed EOM handpiece.

Newly developed modifications of the apparatus and method of the invention as described can prove useful modifications that demonstrate focused hyperthermia treatment of extraocular muscle tendon while preserving safe temperatures in the surrounding tissues. There are two basic questions to be answered for such modifications:

Can a therapeutic hyperthermia dose be delivered to the targeted rectus muscle tendon?

Can the surrounding tissue be protected from overheating?

Modifications of designs of instruments can be tested on excised mammalian eyes. Quantitative measurements of the heat distribution between the electrodes and within the surrounding tissue provide the quantitative data needed for defining the optimal sets of therapeutic variable configurations. For preferred configurations (those giving the greatest ratio between tendon and surround tissue temperatures) histologic studies of the treated tendon and surrounding tissue can be performed to verify the quantitative measurements.

The experimental test protocol, described below, consists of the following stages:

Develop a modified extraocular muscle tendon electrode handset.

Determine the shrinkage vs. temperature function constants for the electrode handset.

Quantify the heat distribution produced by EOM the specific handset.

Determine the shrinkage vs. time functions for the tissue preparation for static and dynamic application of the EOM handset electrodes.

Perform histologic studies of the treated and surround tissue to validate the heat distribution measurements.

Figure 5A:
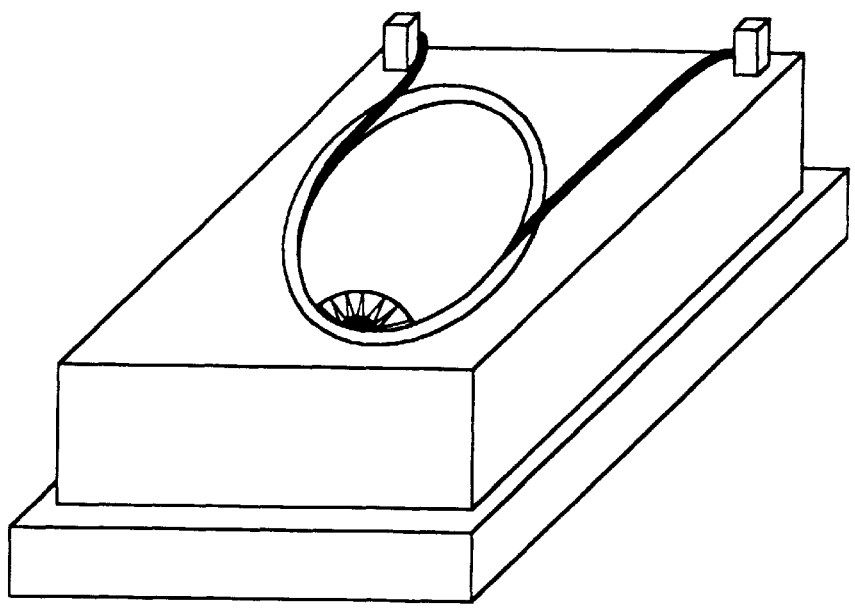
FIG. 5 is a schematic of the ex vivo eye model used for the design of new strabismus bipolar electrodes.
Figure 5B:
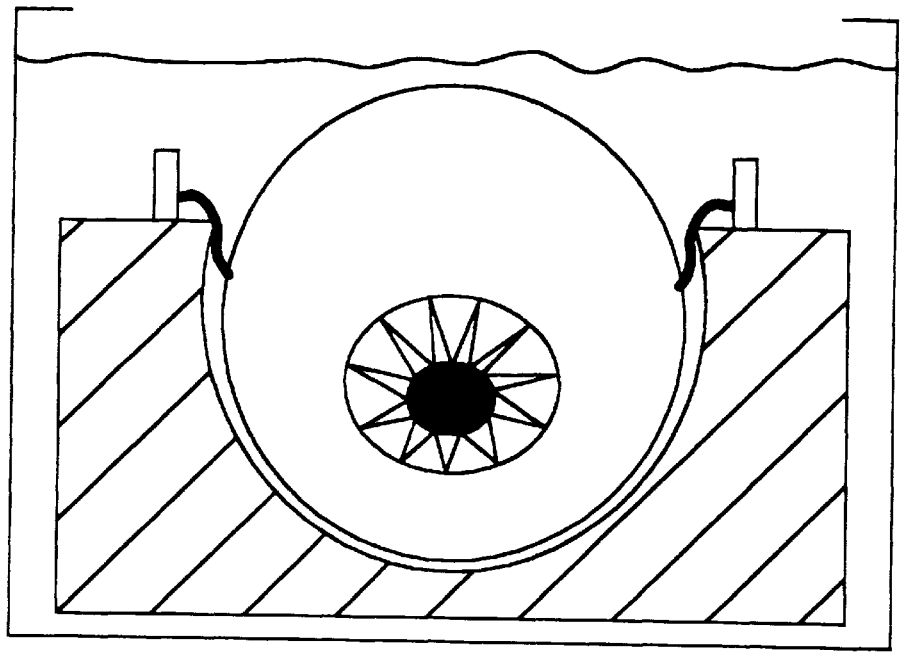

Excised animal eyes can serve as the initial test tissue. The eyes are mounted in a chamber as depicted in FIG. 5 for an ex vivo eye model. One or two rectus muscles is dissected free of the orbital fascia and sutured to corresponding posts on the chamber. The tendon is trimmed to approximate the size of a human tendon.

The saline within the Plexiglas chamber is warmed with a thermostat controlled heating element to 25° C. The eye is submerged in saline within the depression and brought up to 25° C., prior to treatment with the EOM electrode. The preparation will be considered to be at steady state temperature when a vitreal thermocouple records 25° C.

Tissue from several species, which are readily available from various sources, can be used. Typically, access will be available to tissue from experimental animals being sacrificed at neighboring institutions, including young pigs and sheep, as well as from slaughterhouses that will do custom cutting. Whereas the age of the tissue may be a variable in its thermal response, young animals provide the best models, as most strabismus surgery is performed on children. Human cadaver eyes are desired for greater security of test results but their availability is more limited and can be adequately replaced with eyes of lower animals as a given laboratory gains experience with the anatomic adequacy of a lower animal preparation.

Shrinkage versus temperature functions for a particular extraocular muscle preparation can be obtained as described in this specification. The optimal temperature for shrinkage of tendons appears to be about 62° C. for handpieces of the invention and is expected to be similar for most tendons. Shrinkage and temperature functions are used to find the constants, $T_A$, $T_B$, $S_A$, and $S_B$, of the extraocular muscle tendon's shrinkage curve. These constants will be used to establish ranges for independent variables in subsequent experiments in the development of new handpiece electrodes.

A 9-mm long section of the lateral rectus muscle tendon are dissected free of the enucleated eye and trimmed to a width of 9 mm. Reference points (e.g., sutures) are placed on the tissue. The tissue is placed in a saline bath and brought to 25° C. The temperate of the bath is then increased using a thermostat-controlled heater at a rate of 2° C./min. The length of the tendon is recorded on video with simultaneous recording of the bath temperate. The close-up video image is analyzed by measuring the distance between the reference points. Using the results of five successive experiments, shrinkage data is plotted as a function of bath temperature to find the shrinkage curve constants for a particular extraocular muscle tendon tissue preparation.

Figure 6:
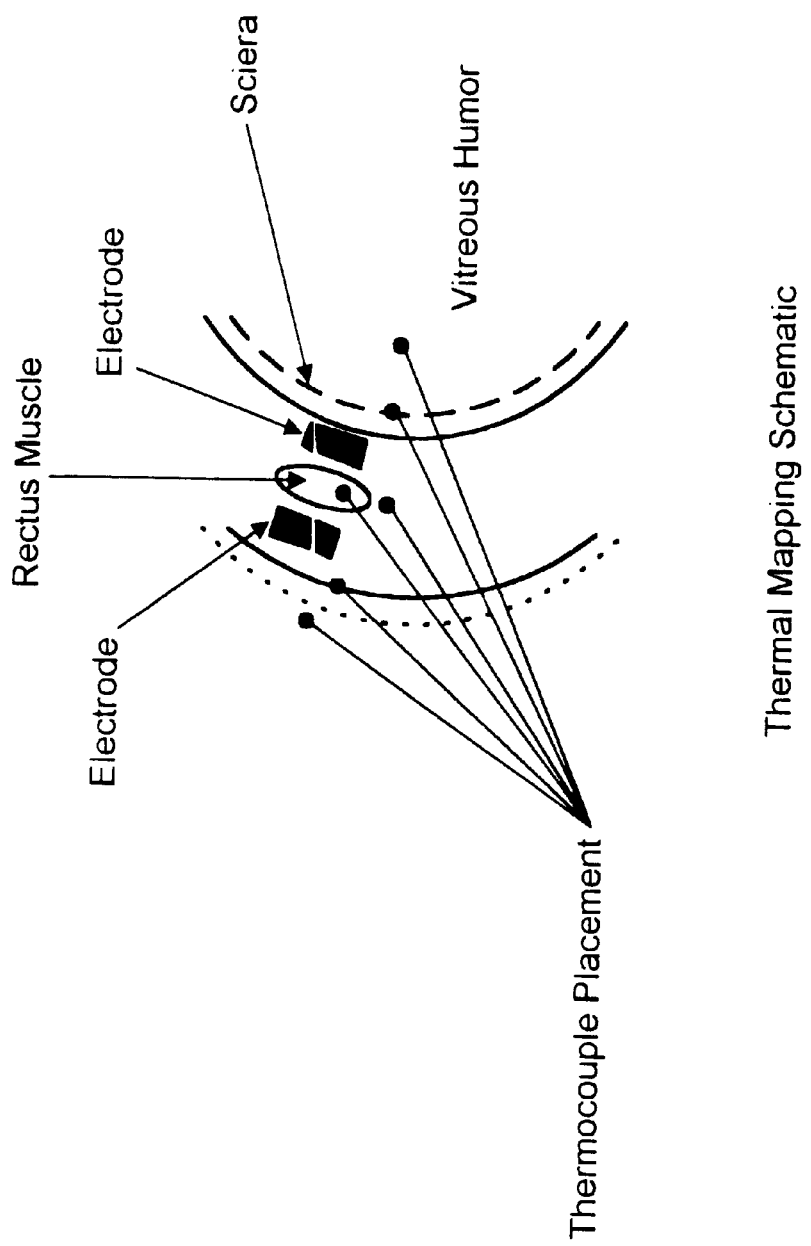
FIG. 6 is a schematic view of placement of thermal measurement instruments for use in design of new strabismus bipolar electrodes.

An experimental protocol is also available to quantify the heat distribution for a given configuration of the therapeutic variables. Needle thermocouples are placed in the tendon site being treated by the EOM electrodes and in the surrounding structures, as shown in FIG. 6. The EOM Tensor is affixed in place with a flexible arm and the RF energy applied. The thermocouple outputs are recorded as a function of time by an automated data logging system.

Temperature versus time functions for each of the thermocouples is plotted for each configuration of the therapeutic variables tested. These functions are compared to each other to identify the optimal therapeutic configuration for a specific electrode handpiece. Steady state values can be expected to be reached in under a minute given the relatively small tissue mass being heated.

Since the thermocouples may act like small heat sinks and low resistance electrical conductors, their presence in the tissue may alter the heat distribution relative to that present in their absence. Therefore, testing is also performed, for promising therapeutic protocols, with the tendon thermocouple absent. If there is a difference in tissue response, a greater RF energy sensitivity in the absence of the thermocouple than in its presence is expected.

Whereas both temperature and treatment time can be used to titrate the therapeutic effect of a new EOM electrode pair, a satisfactory understanding of necessary operating conditions is obtained by acquiring shrinkage vs. time functions for an extraocular muscle-tendon tissue preparation using the thermal conditions generated for selected configurations of the EOM electrodes. Tendon length is monitored by placing reference sutures within the tendon so as to bracket the EOM electrode handpiece. Video pictures of the test preparation can be obtained during the time course of hyperthermia treatment. These video pictures can then be analyzed and the distance between the reference sutures plotted as a function of time.

One test protocol (for determining optimum conditions for a given handpiece) is to use the EOM electrodes in a fixed location, while another desirable test protocol is to use the EOM electrodes while they are moving at a predetermined speed over a (for example) 5 mm distance along the length of the tendon. Because the heat distribution within the tendon is localized within the tissue sandwiched by the EOM electrodes, the shrinkage versus time functions obtained will differ from the uniform heating model.

For new modifications of the fixed location study, the absolute amount of shrinkage is plotted as a function of time for each RF energy level tested. Percent shrinkage is not used as a variable because the tissue is not uniformly heated, and therefore the treated region will be ambiguous. These functions provide dynamic tissue response data that will enable us to establish movement protocols and also understand the results obtained from dynamic administration protocols for any modification of the basic electrode handpiece.

For the EOM electrode movement protocols, the EOM electrode handpiece is placed in a computer-controlled, motor-driven translation stage. The stage moves the handpiece back and forth over a specified distance parallel to the length of the tendon at a predetermined rate. Reference sutures are placed outside the region over which the handpiece is moved. At specified RF energy levels, a series of tendons are treated to derive absolute shrinkage versus time functions. The end points of the treated region may receive a higher therapeutic dose than the midsection due to higher temperatures being reached at these points. To determine the extent of such non-uniformity, reference marks can also be identified within the treated tissue region. Differences in shrinkage are noted. For conditions resulting in more than a 25% difference in shrinkage between end and midsection tissue, non-linear control routines can be implemented to achieve better predictability and greater therapeutic ranges.

Histologic sections of conjunctiva and sclera that are in closest juxtaposition to the treated extraocular muscle tendon site can be examined for hyperthermia exposure for any newly developed handpiece. Histologic conjunctiva and sclera reference sections are obtained by submerging portions of enucleated eyes in a saline bath brought to temperatures ranging from 25° C. to a maximum determined by the results of the thermocouple testing. The maximum bath temperature is set at 25° C. plus two times the highest temperature rise recorded by thermocouples placed in surrounding locations, as described above, during treatment with preferred EOM handpieces and application protocols. Temperature intervals are set to be the greater of 1:0° C. or one fifth of the temperature range. The tissue is kept in the bath for 30 minutes, removed and sectioned. These sections are examined for changes in structure using light microscopy. The higher temperature sections are compared to the 25° C. control sections to delineate heat related changes.

Test tissue sections of conjunctiva and sclera are secured from tissue preparations treated with preferred EOM electrode headpieces and application protocols. The test tissue is prepared in the same manner used to prepare the reference sections and compared to those sections in order to correlate any histological changes noted with temperature. In particular, collagen fiber organization and spacing can be readily studied in this manner.

Histology on dead tissue is less sensitive than histology conducted on living tissue, as subthreshold collagen shrinking temperatures can damage mitochondria and lead to tissue death, and these changes will not be evident in studies of dead tissue. However, the histologic studies described here help to confirm the direct thermocouple measurements for any modification of the handpiece or protocol and provide an early test criterion before moving to in vivo testing.

There are a number of preferred embodiments of the invention. One such preferred embodiment is shown in a series of views in FIGS. 7–9 (in which the numerals designating parts of the apparatus are the same in each of the views), which show a surgical heating probe 100, comprising a handle 10, a radio-frequency-shielded neck 20 extending from the handle and having an unshielded cathode 30 and an unshielded anode 40 present in the neck with a shielded insulating section 50 of the neck located between the cathode and the unshielded anode, the neck being formed so that three points located in the cathode, the anode, and the insulating section, respectively, form a plane, the cathode, the anode, and the insulating section being spaced apart at distances adapted so that cathode 30 and anode 40 can closely approach opposite sides of an extraocular muscle tendon, and an energy connector fixture located in handle 60 and adapted to connect a supply of heating energy 70 to anode 40 and cathode 30. There are no limitations on the manner in which an energy supply is connected to the handpiece of the invention, as this is a conventional aspect of electrical supply and connection to those who commonly practice in this art.

Figure 11:
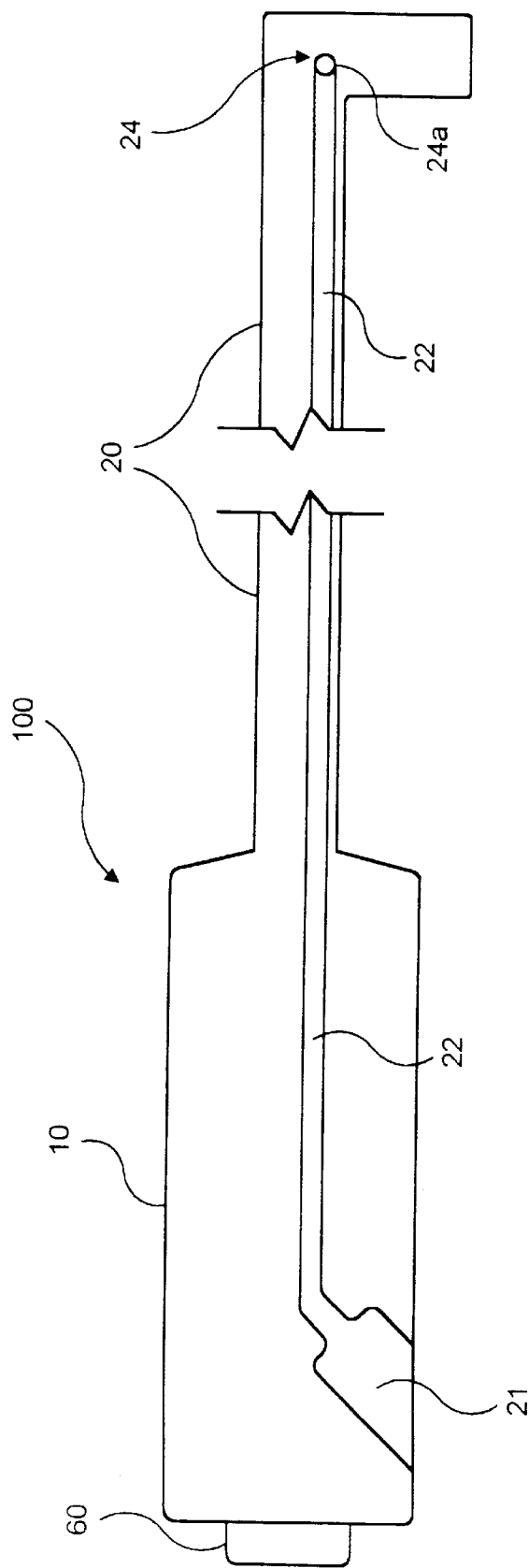
FIG. 11 is a cross-sectional view of a third embodiment having an internal lumen for delivery of a fluid to the heating site.
Figure 12:
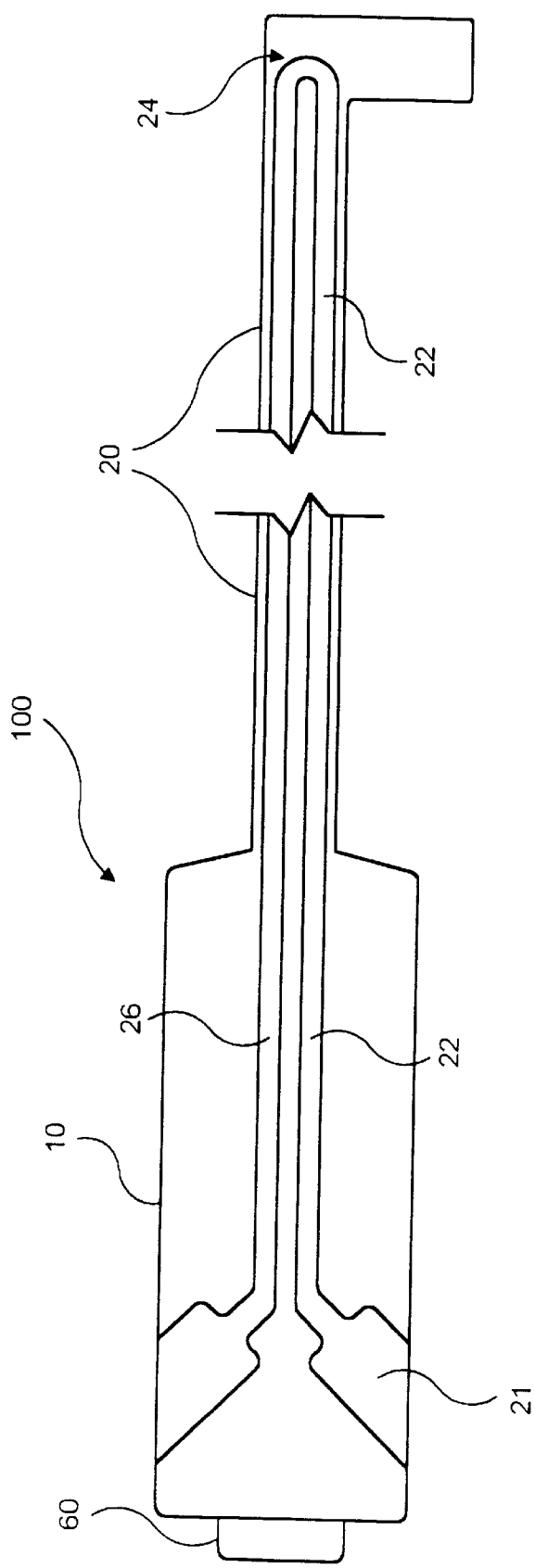
FIG. 12 is a cross-sectional view of a fourth embodiment having internal supply and return lumens for internal cooling.

In some other embodiments the probe comprises an interior hollow lumen 22 that in most cases passes from handle 10 to a location 24 in neck 20 adjacent either cathode 30 or anode 40. In some embodiments lumen 22 has an opening 21 to a first exterior environment (such as a connection to a pump-feed cooling fluid reservoir) at handle 10 and a second opening 24a to the exterior environment (external to the lumen; internal in operation to the ocular cavity) at location in said neck. In other cases lumen 22 is connected to a return lumen 26 at location 24, thereby providing a continuous path for a fluid from handle 10 to and from location 24 in neck 20 thus providing for cooling of the apparatus by recirculating rather than open circulation. An open circuit system is shown in FIG. 11; a closed circuit cooling system is shown in FIG. 12, although a preferred closed circuit cooling system would have lumen 22 connected to return lumen 26 at a location 24 closer to the end of neck 20 for maximum internal cooling.

Preferred probes further comprises a temperature sensor 28, which is preferably located in neck 20 adjacent either the cathode or anode (or both) so that tissue heating can be measured.

Figure 7:
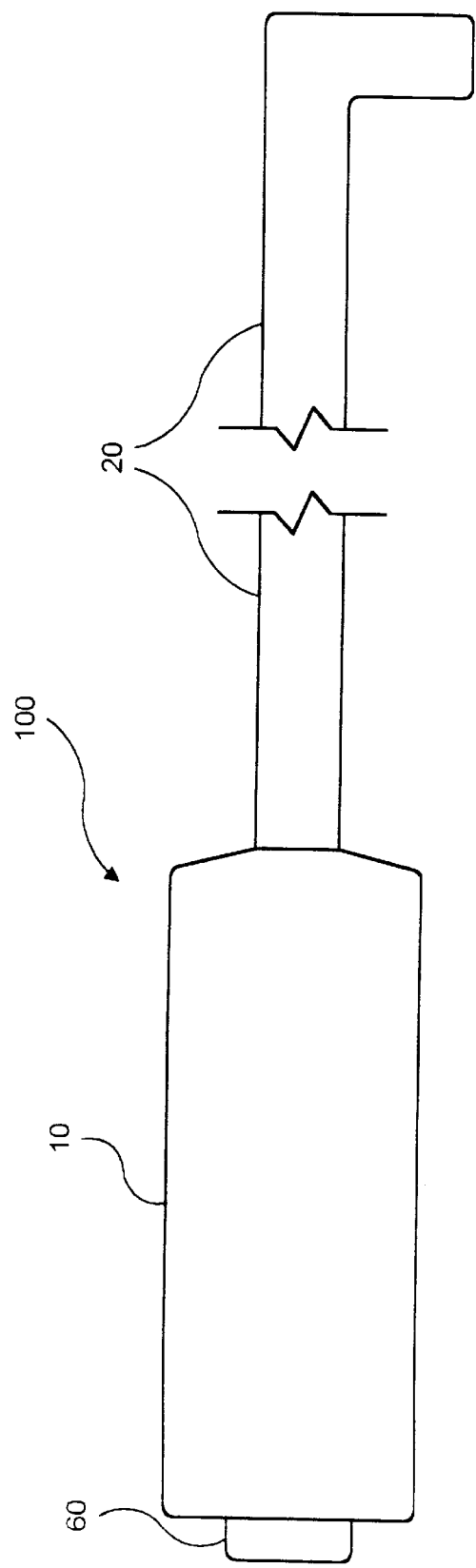
FIGS. 7–9 are planar views in orthogonal planes of a bipolar strabismus electrode of the invention.
Figure 9:
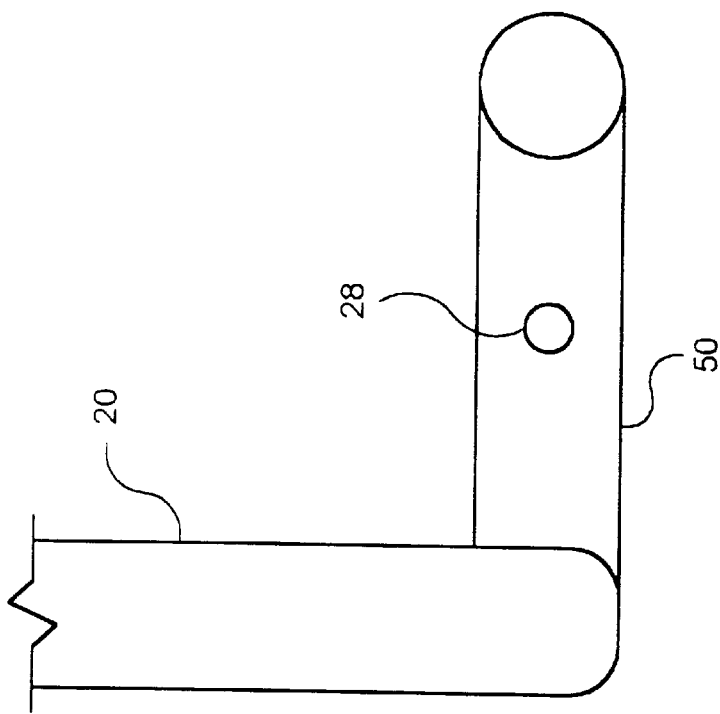
Figure 8:
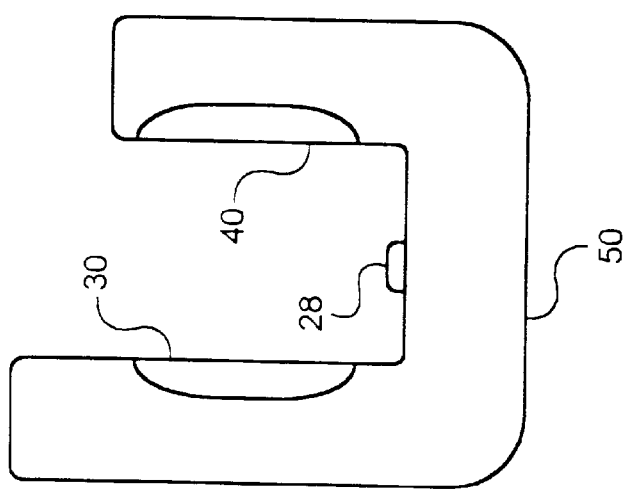

Although the hook-like structure of the handpiece neck is shown at a particular orientation relative to the axis of the neck itself in the embodiment shown in FIGS. 7–9, variations in orientation are possible and provide advantages for different tendons (depending on the direction or directions available for approach to the tendon during surgical operation of the handpiece). If one considers the orientation shown in FIG. 7 to represent depiction of an XY plane with the probe neck extending along an X axis and the descending portion of the neck to be extending along an orthogonal Y axis, then the Z axis will be perpendicular to the plane of view of FIG. 7. FIG. 8 then shows orientation of the "hook" substantially entirely in the YZ plane, with the X axis now being perpendicular to the plane of view of FIG. 8.

In the embodiment shown in FIGS. 7–9, the plane of the "bend" or "hook" region of the probe lies in the YZ plane. In other embodiments, the plane of the hook can be oriented at an angle to the YZ plane depending on the angle between the X axis and the descending portion of the hook (the XY tilt angle), as well as the similar XZ tilt angle. Ninety degree XY and XZ tilt angles give a device formed from parts at right angles to each other, as shown by the embodiment of FIGS. 7–9. An XY tilt angle greater than 90° moves the descending arm of the hook into a more collinear position relative to the axis of the probe neck, gradually resulting in the disappearance of the first angle of the bend at 180° XY tilt angle, which means that for FIGS. 7–9) the plane of the hook would lie entirely in the XZ plane (as shown). An XZ tilt angle greater than 90° (for FIGS. 7–9) moves the plane of the hook into the XY plane when the angle reaches 180°. Angles from 90° to 180° are preferred for both XY and XZ tilt angles.

FIGS. 7–9 (particularly FIG. 8) show a hook portion of the probe neck formed from three substantially straight sections so as to form a U-like structure. As long as appropriate spacing is provided to allow entry and temporary capture of a tendon between the anode and cathode, other shapes of the ascending and descending arms of the hook region are acceptable (such as a V-like structure). The opening of the hook region will preferably be the widest portion of the hook to prevent the hook from snagging during release of the tendon, with continuous narrowing of the hook (or parallel arms) from the opening to the insulated region of the probe neck between the cathode and anode. However, some narrowing at the mouth of the hook region (to help retain the tendon during the heating operation) is acceptable.

Figure 10:
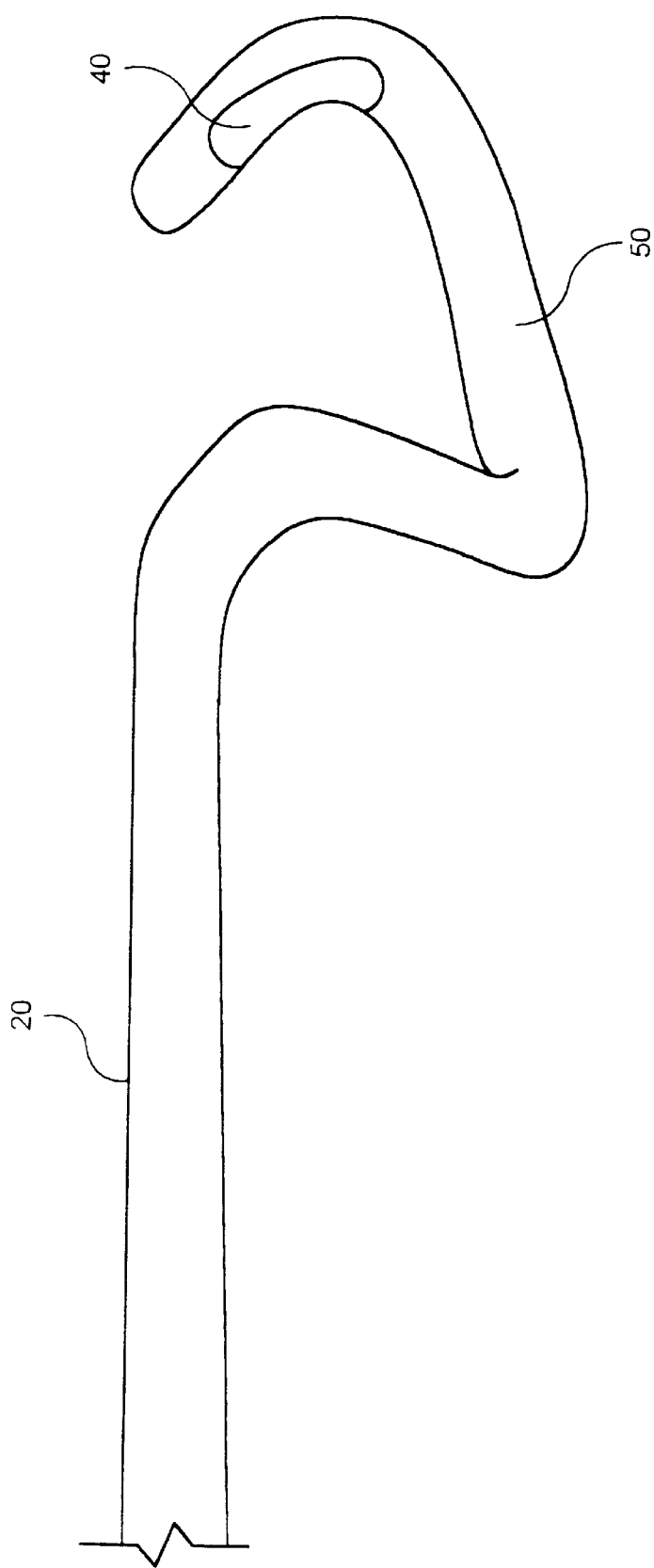
FIG. 10 is a perspective view of another embodiment of a handpiece and electrode of the invention.

It is also possible to have the hook portion of the neck formed in a more complex shape so that not all portions of the ascending, connecting, and descending arms of the hook lie entirely in one plane. Such an embodiment is shown in a perspective view in FIG. 10. In such cases multiple hook planes could be formed by selecting different points in the two electrodes and the insulated intervening section of the probe, so the geometric centers of the electrodes and the insulated intervening section are preferably used as points to define the "plane of the hook" as this phrase is used in the present specification.

In general, the methods of the invention for alleviating strabismus all comprise subjecting a tendon of an eye muscle to heat energy sufficient to shrink collagen in the tendon. Preferred methods further comprise stabilizing the tendon against extension for a time after heating sufficient to allow the heated portion of the tendon to achieve a therapeutically effective resistance to stretching of the heated portion.

Some methods (for example, depending on the desired speed of the operation and the particular apparatus being used) subject at least a portion of a local environment contacting the tendon to a cooling fluid while a portion of the tendon is heated to prevent heat damage to other tissues, as is common in electrosurgical techniques.

LITERATURE CITED

Cosset J M, Brule J M, Salama A M, Damia E, Dutreix J, 1982, Low frequency (0.5 MHz) contact and interstitial techniques for clinical hyperthermia. In: Gautherie M, Albert E (eds) Biomedical Thermology, Liss, New York, pp 649–657.

Crezee J, Lagendijk J J W, 1992, Temperature uniformity during hyperthermia: the impact of large vessels. Phys. Med. Biol., 37:1321–1337.

Danielsen C C, 1981, Thermal stability of reconstituted collagen fibrils. Shrinkage characteristics upon in vitro maturation, Mechanisms of Ageing and Development, 15:269–278.

Danielsen C C, Mosekilde L, Bollerslev J, Moseldlde L, 1994, Thermal Stability of Cortical Bone Collagen and Relation to Age: in Normal Individuals and in Individuals with Osteopetrosis, Bone, 15:91–96.

Fanton G S, Wall M S, 1997, Use of thermal energy in management of shoulder instability, in The unstable shoulder, Warren R F, Craig E V, and Altchek D W (eds) Lippincott-Raven, Philadelphia.

Finger P T, Richards R, Iwamoto T, Myers D B, Jakobiec F A (1987), Heat Shrinkage of Extraocular Muscle Tendon, Arch Ophthalmol, 105:716–718.

Hahn G M, Kernahan P, Martinez A, Pounds D, Prionas S, Anderson T, Justice G, 1980, Some heat transfer problems associated with ultrasound, microwaves or radio frequency. In: Jain R D, Gullino P M (eds) Thermal characteristics of tumors: applications to detection and treatment. Ann NY Acad Sci 335:327.

McCotter R E, Fralick F B, Henderson J W, 1949, A Comprehensive Description of the Orbit, Orbital Content, and Associated Structures with Clinical Applications, American Academy of Ophthalmology and Otolaryngology.

National Advisory Eye Council, 1994, Vision Research, A National Plan: 1994–1998, A Report of the National Advisory Eye Council, U.S. Department of Health and Human Services, Public Health Service, National Institutes of Health, National Eye Institute.

Spooner, J D, 1957, Ocular Anatomy, The Hatton Press, Ltd., London and Hereford.

Strohbehn J W, 1983, Temperature distributions from interstitial RF electrode hyperthermia systems: Theoretical predictions, Int. J. Radiation Oncology Biol. Phys, 9:1655–1667.

Mechling J A, Strohbehn, 1986, A theoretical comparison of the temperature distributions produced by three interstitial hyperthermia systems, Int. J. Radiation Oncology Biol. Phys. 12:2137–2149.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A surgical heating probe, comprising:
   a handle,
   a radio-frequency-shielded neck extending from the handle, the neck forming a hook shaped member having an unshielded cathode and an unshielded anode on opposing arms of the hook shaped member with a gap therebetween, the neck including a bent region between the cathode and anode which comprises a shielded insulating section and causes the cathode and anode to be positioned on opposite sides of the gap between the cathode and anode, and
   an energy connector fixture located in said handle and adapted to connect a supply of heating energy to the anode and the cathode.

2. The probe of claim 1, wherein the probe comprises an interior hollow lumen.

3. The probe of claim 2, wherein the lumen passes from the handle to a location in the neck adjacent either the cathode or the anode.

4. The probe of claim 3, wherein the lumen is open to a first exterior environment at the handle and a second exterior environment at the location in the neck.

5. The probe of claim 3, wherein the lumen is connected to a return lumen at the location in the neck to provide a continuous path for a fluid from the handle to and from the location in the neck.

6. The probe of claim 1, wherein the probe further comprises a temperature sensor.

7. The probe of claim 6, wherein the temperature sensor is located in the neck adjacent either the cathode or the anode.

8. A method of alleviating strabismus, comprising:
   taking a hook shaped member having an unshielded cathode and an unshielded anode on opposing arms of the hook shaped member with a gap therebetween;
   placing a tendon of an eye muscle in the gap between the cathode and anode; and
   delivering radio-frequency energy to the tendon sufficient to shrink collagen in the tendon.

9. The method of claim 8, wherein the method further comprises stabilizing the tendon against extension for a time after the heating sufficient to allow the portion of the tendon to achieve a therapeutically effective resistance to stretching of the heated portion.

10. The method of claim 8, wherein at least a portion of a local environment contacting the tendon is cooled while the portion of the tendon is heated.

\* \* \* \* \*

UNITED STATES PATENT AND TRADEMARK OFFICE
CERTIFICATE OF CORRECTION

PATENT NO.   : 6,246,913 B1
DATED        : June 12, 2001
INVENTOR(S)  : Hugh R. Sharkey It is certified that error appears in the above-identified patent and that said Letters Patent is hereby corrected as shown below:

<u>Title page,</u>
Item [73], should read, -- Assignee: Oratec Interventions, Inc., Menlo Park, Ca (US) --

Signed and Sealed this

Eighteenth Day of June, 2002

Attest:

JAMES E. ROGAN
Attesting Officer
Director of the United States Patent and Trademark Office